United States Patent
Kaur et al.

(10) Patent No.: US 8,609,428 B2
(45) Date of Patent: Dec. 17, 2013

(54) COLORIMETRIC ASSAY FOR PYRETHROID INSECTICIDES ON SOLID ITEMS

(75) Inventors: Harparkash Kaur, London (GB); Teunis Eggelte, Amsterdam (NL)

(73) Assignee: London School of Hygiene & Tropical Medicine, London (GB)

( * ) Notice: Subject to any disclaimer, the term of this patent is extended or adjusted under 35 U.S.C. 154(b) by 189 days.

(21) Appl. No.: 12/919,947

(22) PCT Filed: Feb. 27, 2009

(86) PCT No.: PCT/GB2009/000554
§ 371 (c)(1), (2), (4) Date: Oct. 14, 2010

(87) PCT Pub. No.: WO2009/106845
PCT Pub. Date: Sep. 3, 2009

(65) Prior Publication Data
US 2011/0033945 A1  Feb. 10, 2011

(30) Foreign Application Priority Data
Feb. 29, 2008 (GB) .................................. 0803850.7

(51) Int. Cl.
*G01N 33/00* (2006.01)

(52) U.S. Cl.
USPC ........... 436/128; 436/106; 436/109; 436/127; 436/164; 436/166

(58) Field of Classification Search
USPC ................. 436/106, 109, 127–128, 164, 166
See application file for complete search history.

(56) References Cited

U.S. PATENT DOCUMENTS

| | | | | |
|---|---|---|---|---|
| 3,910,763 A | * | 10/1975 | Poziomek et al. | 436/104 |
| 4,012,286 A | * | 3/1977 | Sanderson et al. | 435/14 |
| 4,223,090 A | * | 9/1980 | Mazza | 435/19 |
| 4,227,888 A | * | 10/1980 | Rueppel et al. | 436/109 |
| 4,971,762 A | * | 11/1990 | Bather | 422/401 |
| 5,108,900 A | * | 4/1992 | Stanker et al. | 435/7.93 |
| 5,124,141 A | * | 6/1992 | Makler | 435/26 |
| 5,294,540 A | * | 3/1994 | Daniel et al. | 435/25 |
| 5,723,306 A | * | 3/1998 | Pullen et al. | 435/7.93 |
| 6,617,123 B1 | * | 9/2003 | Smith | 435/19 |
| 2003/0207344 A1 | * | 11/2003 | Hammock et al. | 435/18 |
| 2004/0014195 A1 | * | 1/2004 | DeSantis et al. | 435/228 |
| 2004/0038419 A1 | * | 2/2004 | Weiner et al. | 436/109 |
| 2005/0176117 A1 | * | 8/2005 | Russell et al. | 435/128 |
| 2008/0227746 A1 | * | 9/2008 | Boss et al. | 514/52 |

FOREIGN PATENT DOCUMENTS

WO   WO 03/031966 A1   4/2003

OTHER PUBLICATIONS

Guilbault, G. G. et al, Analytical Chemistry 1966, 38, 834-836.*
Kramer, D. N. et al, Journal of Organic Chemistry 1967, 32, 1163-1165.*
Gewitz, H.-S. et al, Planta 1976, 131, 145-148.*
Baker, J. K., Analytical Chemistry 1982, 54, 347-349.*
Gupta, S. et al, Analytical Communications 1996, 33, 239-240.*
Gupta, S. et al, Talanta 1998, 45, 1111-1114.*
Enayati, A. A. et al, Transactions of the Royal Society of Tropical Medicine and Hygiene 2005, 99, 369-378.*
Vesey, C. J. et al, Annals of Clinical Biochemistry 1999, 36, 755-758.*
Sakuragawa, A. et al, Bunseki Kagaku 1991, 40, T41-T46.*
Sinha, C. et al, Neurotoxicology and Teratology 2006, 28, 472-481.*
Erlanger et al., "Field Issues Related to Effectiveness of Insecticide-Treated Nets in Tanzania," *Med. Vet. Entomol.* 18:153-160, 2004.

* cited by examiner

*Primary Examiner* — Arlen Soderquist
(74) *Attorney, Agent, or Firm* — Klarquist Sparkman, LLP

(57) ABSTRACT

The invention relates to an assay to test for pyrethroids in a sample. The assay is particularly useful for testing material treated with pyrethroids, such as bed netting and the like.

10 Claims, No Drawings

COLORIMETRIC ASSAY FOR PYRETHROID INSECTICIDES ON SOLID ITEMS

CROSS REFERENCE TO RELATED APPLICATIONS

This is the U.S. National Stage of International Application No. PCT/GB2009/000554 filed Feb. 27, 2009, which was published in English under PCT Article 21(2), which in turn claims the benefit of Great Britain Application No. 0803850.7, filed Feb. 29, 2008.

The invention relates to a method for detecting the presence of type II-pyrethroids, especially on bed nets and sprayed walls.

Insecticide treated nets (ITNs) and indoor residual spraying (IRS) of insecticides are used as the major modes of intervention in the fight against malaria. Measuring the actual amount of deposits of insecticides on the bed nets and on the walls is essential for evaluation of quality control of the applied intervention as per instruction. Currently such information can only be provided by costly and sophisticated gas chromatography [1, 2], high performance liquid chromatography [3] techniques which are not readily available and at present cannot be used in the field without setting up an analytical laboratory. Other methods include bioassays where insecticide susceptible strains of mosquitoes are exposed to the impregnated netting material using WHO bioassay kits such as cones or tubes. These bioassays can reveal the residual activity of the insecticide remaining on the net and indirectly can be used to estimate the quality of the treatment on the net, i.e. does it still kill the mosquitoes [4]. Bioassays are technically demanding to perform and require skilled staff with access to laboratory and insectary facilities. It is also very difficult to perform bioassays on nets in situ and require for the nets to be removed from the homes for this method of determination.

Generally the monitoring of bed net impregnation is restricted to reports from health staff and questioning the net users. There is hence a need for suitable field friendly/cost effective tests that can be carried out by non specialist persons. A simple test should help to determine the amount of insecticide on the nets and compliance of IRS.

The inventors have developed a rapid and simple method for extracting insecticide from, for example, bed nets or sprayed walls, and for colorimetrically confirming the presence of the insecticide.

Type II pyrethroids are a class of pyrethroids which contain an alpha cyano ester group, obtained by esterification of a cyanohydrine, often m-phenoxy benzaldehyd cyanohydrine, with a modified pyrethroic acid derivative. Examples of such pyrethroids are cypermethrin, deltamethrin and cyhalothrin. Under basic conditions these type II pyrethroids are easily hydrolyzed resulting in the formation of pyrethroic acid derivative, m-phenoxybenzaldehyde and cyanide. A test to detect the type II pyrethroids has been developed on basis of the formation and detection of cyanide upon hydrolysis of the type II pyrethroids.

The test is based on the detection of free cyanide obtained by hydrolysis of an alfa cyano pyrethroid. Free cyanide can react with an aromatic aldehyde to form a cyanohydrin. When the aromatic aldehyde is substituted with electron withdrawing group(s) an electron transfer reaction can occur if the second compound is a suitable acceptor. In the reaction a hydride is transferred from the cyanohydrine to a hydride acceptor molecule which is then reduced. This process can be followed through the change of physical properties of the hydride acceptor molecule. In the process an acylcyanide is formed from the aromatic aldehyde. Under basic conditions this will be hydrolyzed and cyanide released, which on its turn can re-enter into the hydride transfer reaction.

According to the invention, there is provided a method for detecting the presence of a type II pyrethroid in a sample, comprising the steps of adding a base to the sample, adding a mixture of a hydride donor and a hydride acceptor to the sample and observing the sample for a colour change. As the test is based on the detection of cyanide generated from the type II pyrethroid, the test is therefore also applicable to substances organic or inorganic which can release cyanide.

The base may be any base, usually a solution of a hydroxide in water or in a solvent/water mixture. The concentration of the base will depend upon the other reagents used, but will generally be in the range of 0.1 to 1000 mM.

The terms hydride donor and hydride acceptor are well known in the art. Any hydride donor or hydride acceptor may be used. The donor and acceptor may be two different compounds, or in some circumstances the same compound may act as both the donor and the acceptor. Examples of hydride donors include aromatic aldehydes, especially those substituted with one or more electron withdrawing groups such as nitro, cyano, trimethylsulfonyl and trihalomethylsulfonyl groups. The preferred position on a molecule of the electron withdrawing group is in the para position. Examples of hydride donors include para-nitrobenzaldehyde, para-cyanobenzaldehyde, and para-methylsulphonylbenzaldehyde.

Hydride acceptor compounds include compounds such as substituted nitro aromatics in which the substituent is an electron withdrawing group in an ortho or para position. Such compounds include para-nitrobenzaldehyde, 1,2-dintrobenzene, 1,4-dinitrobenzene and 4,5-dinitrobenzoic acid. Also useful as hydride acceptors are tetrazolium salts.

Tetrazolium salts eg Triphenyl tetrazolium chloride, Tetratzolium Blue, Nitrotetrazolium Blue, Iodo-nitro tetrazolium, Tetrazolium Violet, WST-1.

The optimal concentrations of the components of the reagents are dependent on the choice of the hydride donor and acceptor compounds in the range of 1-1000 mM and 1-500 mM respectively.

A pyrethroid is a synthetic form of a pyrethrin. The term is well known in the art. Type II pyrethroids include, for example, cypermethrin, cyfluthrin, cyhalothrin, deltamethrin, cyphenothrin, fenvalerate and fluvalinate. Preferred type II pyrethroids include deltamethrin, α-cypermethrin and λ-cyhalothrin.

The sample may be any sample in which a pyrethroid may be found. For example, the sample may be a solution of the pyrethroid, or may be a sample of, or obtained from an item treated with the pyrethroid. In particular, the sample may be bed netting or may be a wall onto which the pyrethroid may have been sprayed. Further, the sample could be a swab obtained from such an item. Where the sample is an item that could have been impregnated or sprayed with a pyrethroid, the method preferably includes the step of extracting the pyrethroid with an organic solvent. The solvent is preferably added to the sample prior to or simultaneously with the hydride donor and acceptor. Any solvent may be used; providing it is able to extract the pyrethroid and dissolve the reagents and is miscible with an aqueous base solution, Examples of solvents include acetonitrile, methanol, ethanol, isopropanol, methoxyethanol ethoxyethanol, tetrahydrofuran, dioxane, dimethylformamide, dimethylacetamide, dimethylsulfoxide, 2-pyrrolidone and N-methyl 2-pyrrolidone.

The reagents and solvent, where used, may be added to the sample in any appropriate way. For example, they may be sprayed onto the sample, or the sample dipped into vessels containing each of the reagents and solvent.

When the sample is, itself coloured, it is possible that the colour of the sample will interfere with the colour change seen when adding the reagents. Accordingly, it may be necessary to dilute the sample following addition of the solvent. Alternatively, it is possible to subtract the absorption of the colour of the sample from the reaction product, using a spectrophotometer e.g microtitre plate reader It may be desirable to stop the reaction following the addition of the reagents. In that case, the method may also comprise the step of stopping the reaction by addition of an acid solution. The acid can either be an organic acid e.g. acetic acid or a mineral acid e.g. HCl.

As indicated above, when a type II pyrethroid is present, the sample changes colour. When para-nitrobenzaldehyde and 1,2-dinitrobenzene are used, the colour change is to violet. The term violet is used to mean any colour having a wavelength of 500 nm to 600 nm, more preferably 520 nm to 580 nm, more preferably 540 to 570 nm.

The invention will now be described in detail, by way of example only.

Hydride Transfer Reactions.

Hydride transfer reactions from aromatic aldehydes are well known in the chemical literature. The reaction of benzaldehyde with hydroxide is such an example, the so called Cannizzaro reaction, in which a hydride is transferred to a second molecule benzaldehyde is reduced and benzoic acid and benzylalcohol are formed in the reaction. Reaction of aromatic aldehydes with cyanide result generally in the formation of benzoin compounds via a cyanohydrin intermediate which can react with another molecule of aromatic aldehyde. to form a benzoin termed the benzoin condensation. In the overall reaction cyanide acts as a catalyst and is not found the end product. Not all aromatic aldehydes will lead to products of benzoin condensation in the presence of cyanide. In case of certain substituted aromatic aldehydes hydride transfer reactions can occur from the cyanohydrin intermediate in a process comparable to that seen in the Cannizzaro reaction. When a better hydride acceptor than the aromatic aldehyde is present in the system this compound will be reduced in stead of a second molecule of aromatic aldehyde. In the process an aromatic acylcyanide is formed which will be hydrolyzed under the reaction conditions to give an aromatic carboxylic acid and cyanide. The latter can start a new cycle of reactions and cyanide acts therefore as a catalyst.

The types of aldehydes which will enter into hydride transfer reactions are aromatic aldehydes such as the benzaldhydes that are substituted with one or more electron withdrawing groups e.g. nitro, cyano, trimetylsulfonyl, trihalomethylsulfonyl in particular those in which the electron with drawing group is in a para position in relation to the aldehyde group.

The hydride (electron) acceptor molecule can be of any class of compounds that can function as such and give a change in properties that can be easily measured. A type of compounds that can be used are substituted nitro aromatics in which the substituent is an electron with drawing group in particular a nitro group in an ortho or para position e.g. 1,2 and 1,4-dinitrobenzene and related compounds.

Hydride transfer to a nitro group results first in the formation of a nitroso group, which then undergo a second hydride transfer shift to be converted into a hydroxylamino group. In the case of 1,2 and 1,4 dintrobenzene a reaction with hydroxide can occur with the formation of highly coloured products. In case of 1,2-dinitrobenzene the maximum is at 560 nm.

Alternatively the hydroxylamino compound can react with the nitroso compound and/or the aromatic aldehyde used as a hydride donor in the test to give the coloured product. In the case when the aromatic aldehyde which acts as hydride donor is substituted with a nitro group this can enter the reaction also as the hydride acceptor in the absence of another hydride acceptor. The appearance of a colour depends on the solvents and the concentration of the base used (pH) in the test.

Another class of hydride acceptors is the so called tetrazolium compounds. Upon reduction by a hydride highly coloured products (formazans) are formed. These hydride acceptors may be a tetrazolium salt that will give insoluble formazans as well as tetrazolium salts which have been designed to provide water soluble formazans.

The hydride transfer reaction are dependable on the solvent used, the amount of water in the system and the strength of the base (pH). Solvents should be of a type that is miscible with water.

The pH in the test system should be sufficiently high to effect hydrolysis of the type II. pyrethroid and optimal for the hydride transfer reaction. The optimal pH will depend on the choice of the hydride donor and acceptor molecules.

General Procedure:

To a piece of bed net in a tube is added x µl of a solvent, followed by x µl of a hydride donor compound and x µl of a hydride acceptor in the same solvent (or reverse order of addition of the reagents) and finally x µl base solution in water is added. The solution will start to colour when the bed net was impregnated with a type II pyrethroid.

The depth of colour seen is dependent on the amount of type II pyrethroids released from the bed net. Alternatively a swap of the bed net or of a sprayed surface can be made and processed in a similar manner.

EXAMPLE 1

To a piece of bed net in a tube is added 200 µl methanol, 200 µl 200 mM p-nitrobenzaldehyde and 200 µl 100 mM 1,2-dinitrobenzene in methanol. Upon addition of 200 µl 125 mM aqueous NaOH solution will start to colour violet in presence of a type II pyrethroid.

EXAMPLE 2

To a piece of bed net in a tube is added 600 µl a solution of para nitrobenzaldehyde (100 mM) in acetonitril followed by 200 µl of a 50 mM aqueous NaOH solution. A pink colour wills start to appear.

EXAMPLE 3

To a piece of bed net in a tube is added 200 µl of ethanol, 200 µl of 200 mM para cyanobenzaldehyde, 200 µl Tetrazolium in ethanol Violet and finally 200 µl of 10 mM aqueous NaOH. A purple colour will start to appear.

EXAMPLE 4

To a piece of bed net in a tube is added 200 µl methoxyethanol, 200 µl 200 mM p-nitrobenzaldehyde and 200 µl 100 mM 1,2-dinitrobenzene in methoxy-ethanol. Upon addition of 200 µl 125 mM aqueous NaOH solution will start to colour violet in presence of a type II pyrethroid.

EXAMPLE 5

Detection of Pyrethroids

Solutions containing various pyrethroid standards were treated with reagent I (NaOH) followed by reagent II (a solution of para nitrobenzaldehyde and 1,2-dinitrobenzene) which results in the production of the violet colour. Reagents I and II can also be added in reverse order. The rapid formation of a violet colour with deltamethrin, α-cypermethrin, λ-cyhalothrin but not with permethrin, indicates that the α-cyanopyrethoids currently used for impregnation of bednets are detected in this test.

The absorption curve of the reaction product formed has a maximum at about 560 nm. The violet colour enables for ease of visual assessment of the results. i.e the deeper the colour correlates to the amount of pyrethroid.

The test can also be performed in 96-wells microtitre plates and enabling for the concentration of the test extract to be determined using a microtitreplate reader. The extinction can be measured over a broad range of wavelengths (500-600 nm) without great loss of sensitivity using the standard range of filters found on the plate reader without the need to purchase special filters. When the reaction is stopped by addition of acid a change in colour may be seen which can be measured at the appropriate wavelength. The colour produced is matching for all the pyrethroids tested and furthermore the values obtained from the plate reader confirmed that the response of the test is the same for DM, α-Cypermethrin and λ-Cyhalothrin but permethrin was not detected.

EXAMPLE 6

Efficiency of Extraction of Deltamethrin from a Sample.

Various organic solvents and conditions of hydrolysis was undertaken to establish the optimum conditions for this process using bed nets with deltamethrin. Experiments were then carried out using the nets to determine the best solvent for the whole procedure i.e. extraction and colour reaction. These nets were also analysed by HPLC.

Bed nets were cut (2.5×2.5 cm and each net was extracted into 500 μl of solvents [A-E], 50 μl of this extract was used for the colorimetric test and the rest was subjected to HPLC analyses injecting 20 μl on the column).

Deltamethrin was not extracted from net sample no 51 but showed the formation of the purple colour when treated with the test reagents. On consultation with the description of the samples it was realised that sample 51 had not been treated with deltamethrin (hence seen as no value indicated) but has α-cypermethrin on it. On re-examining the HPLC chromatogram the peak detected was confirmed as α-cypermethrin. This latter pyrethroid indicates a faint reaction in solvent A, better with solvents C, D and E but nothing with solvent B.

Results of the HPLC analyses confirm the necessity for optimisation of the solvents for the extraction of the various insecticides from bed nets will have to be compatible with the conditions used in the test. Some solvents will have an influence the colorimetric reaction.

EXAMPLE 7

Suitability of the Test to be Used in a Test Tube and Microtitre Plates

Net samples were used to demonstrate the suitability of either test tubes or microtitre plates. Each bed net sample (2.5×2.5 cm) was extracted in solvent A (2 ml) which had been found to be the most efficient for the extraction of DM. Known amounts of DM were also used in the microtitre plate to indicate the possible semi-quantitative nature of the test.
To Demonstrate the Suitability of the Test in Test Tubes:
A 100 μl of the above net extract was placed in the test tube followed by the addition of reagent mixture I (200 μl) and then reagent II (100 μl).
To Demonstrate the Suitability of the Test Using Microtitre Plates:
Known concentrations of DM (0-62.25 μg/ml; 25 μl) and extracts (25 μl each) of the above net were placed in each well of the microtitre plate. Then reagent mixture I (50 μl) was added to each well followed by reagent II (25 μl) and the colour produced was read using the plate reader.
To Demonstrate the Suitable Time Period to Measure the Depth of Colour Using a Plate Reader:
The above plate was monitored after 15 and 30 mins to obtain a measure of colour formed with known amounts of DM (μg/ml).
Experiment Carried Out Find Out the Effect of Volume of Extract Used with the Same Amount of Reagents I and II ie does Using Twice the Amount of Extract Result in a Deeper Colour. Is the Test Sensitive Enough to Overcome Interference from Extracted Dyes:

Many bed nets are brightly coloured and it is important to know whether the dyes will interfere with the test. The dye from many coloured nets does not come off when an organic solvent is used to extract the DM. However in other cases the dye will also be extracted with the DM during the extraction procedure needed in this test this will interfere with the colorimetric reaction of the test. Often the extract of a brightly coloured net is colourless but when the dye is extracted there are two options. One can dilute the extract solution resulting in less interference from the dye if the sensitivity of the test is sufficient to allow for further dilution of the sample and or one can also subtract the absorption from that of the reaction product which necessities the use of a microtitre plate reader.

The sensitivity of the test will depend on factors such as the size of the net sample, the volume of the solvent used to extract that sample and the quantity of the sample extract used in the test system. 25 μl and 50 μl samples of the extract described above were treated with reagent mixture I (50 μl) followed by reagent II (25 μl) in each well.

EXAMPLE 8

Establishing the Linear Range of the Test for Three Representative Type II Pyrethroids (Deltamethrin, Lambda Cyhalothrin, Cypermenthrin).

Linearity of colour formation was explored using analytical standards and HPLC characterised ITN extracts, i.e. relationship between the depth of colour and amount of pyrethroid.

The formation of the colour was shown to be directly proportional to the concentration of DM at any moment up to 60 min after initiating the test reaction as measured at 544 nm using a microtitre plate reader.

EXAMPLE 9

Testing Degradation Products of Pyrethroids.

The inventors were able to purchase and test a number of other known degradation products of pyrethroids. These products did not react in the test.

EXAMPLE 10

Testing for False Positives

The inventors explored the probability of false positives from other things possibly present on the insecticide treated material (e.g. soap used in washing, formulation additives, paraffin, charcoal etc) in a number of HPLC characterised extracts As bed nets will undergo many washes, we tested the effect of a standard soap and looked for any loss of colour in the presence of a WHO specified soap that is used to wash the nets. We also carried out the reaction in the presence of a binding agent (Bayer) that is used to impregnate the bed nets with deltamethrin. Theoretically this binding agent could have an influence on the initiation of the reaction. There is no interference in the depth of colour with DM in presence of the soap or the binder.

EXAMPLE 11

Selection of Solvents

Different solvents were tested for their ability to extract the pyrethroids. FIG. 14 shows results of testing a series of DM standards in test tube experiments. Commercial DM dissolved in solvent B was placed in test tubes (100 μl each) at known concentrations. Then reagent mixture I (200 μl) was added to each tube followed by reagent II (100 μl). The formation of colour was recorded at the given time intervals above.

EXAMPLE 12

Change of Colour with Time:

The violet colour of the reaction product increases in time during 30-60 min but is not stable and was found to change with time. It changed from violet into an orange colour overnight.

EXAMPLE 13

Stopping the Reaction:

Intensity of the colour will continue to increase in time. This is due to the catalytic nature of the reaction and the reason why a very sensitive test is obtained. The inventors have thus developed a way stop the reaction in order to be able to measure the colour formation at any given moment in time.

This has been achieved by adding a third reagent (an acid) to the incubation mixture which stops the reaction and result in a change in the colour from violet to yellow, which can be measured at λ=450 nm. Filters necessary for this colour are standard accessories of microtitre plate readers. Using this procedure the absorption value (O.D) measured at 450 nm is about half of that of the one measured at 544 nm before stopping the reaction. The colour is stable and still visible a week after stopping the reaction by adding reagent III.

Extracts of the 20 blind net samples were used to demonstrate that the reaction can be stopped at a specific time.

EXAMPLE 14

Applying the Test to Bed Net Samples:

The inventors tested 20 samples from the bed nets, noting the colour of the net, the colour that is extracted into solvent A and finally the amount of DM measured by HPLC. Solvent A was used in this analysis. The results are shown in table 1. The table shows the identity of the samples our arbitrary numbers, colour of the net, colour produced upon extraction into solvent A and finally the amount of DM detected. The amount of DM in bold is as measured on the plate reader after extraction with solvent B and the amount in brackets is that extracted into solvent A and measured on HPLC. The amount of DM varies as detected by the two methods is due to the use of different solvents used for the extraction process. Net no 8568 indicates it might not be DM.

EXAMPLE 15

A piece of bed net is positioned at the bottom of a tube and to the tube are added 200 μl of a solvent A, 400 μl of a mixture of a substituted benzaldehyde e.g para nitrobenzaldehyde, para cyanobenzaldehyde in solvent A and 200 μl of a base solution. A colour starts to appear and after an appropriate time period 200 μl of an acid solution is added to stop the reaction.

TABLE 1

| Net No | Arbitrary No | Colour of net | Extracted colour in reagent A | DM mg/m2 |
| --- | --- | --- | --- | --- |
| 1065 | 1 | Blue | Colourless | 76.0 (95.0) |
| 1114 | 2 | Green | Colourless | 17.0 (38.0) |
| 1324 | 3 | Green | Faint green | 40.0 (45.0) |
| 2532 | 4 | White | Colourless | 10.0 (3.0) |
| 2627 | 5 | Henna green | Reddish brown | 3.0 (40.0) |
| 2700 | 6 | White | Colourless | 4.0 (6.0) |
| 2911 | 7 | Blue | Colourless | 59.0 (57.0) |
| 3867 | 8 | Henna green | Yellow | 2.0 (Not detected) |
| 4022 | 9 | White | Colourless | 52.0 (67.0) |
| 4512 | 10 | White | Colourless | 5.0 (7.0) |
| 6432 | 11 | Turquoise | Colourless | Not detected (5.0) |
| 6489 | 12 | Green | Florescent green | 138.0 (118.0) |
| 7457 | 13 | White | Colourless | 27.0 (42.0) |
| 7685 | 14 | White | Colourless | 18.0 (25.0) |
| 7827 | 15 | White | Colourless | Not detected (Not detected) |
| 8564 | 16 | Green | Florescent green | Not detected (Not detected) |
| 8568 | 17 | Green | Colourless | 10.0 (Not detected) |
| 8759 | 18 | White | Colourless | 12.0 (21.0) |
| 8865 | 19 | Green | Florescent green | 42.0 (47.0) |
| 9642 | 20 | Henna green | Very faint brown | 13.0 (9.0) |

The invention claimed is:

1. A solution-based method for detecting the presence of a type II pyrethroid in a solid item possibly impregnated or sprayed with a type II pyrethroid, comprising:
   adding a solution comprising a base, a solvent, and water to a vessel containing a solid item possibly impregnated or sprayed with a type II pyrethroid;
   adding a mixture of a hydride donor and a hydride acceptor to the vessel containing the solid item; and
   observing contents in the vessel containing the solid item for a colour change indicating presence of a type II pyrethroid in the sample.

2. The method of claim 1, wherein the hydride donor is para-nitrobenzaldehyde or para-cyanobenzaldehyde.

3. The method of claim 1, wherein the hydride acceptor is a dintrobenzene or a tetrazolium salt.

4. The method of claim 1, further comprising extracting the type II pyrethroid with a solvent.

5. The method of claim 1, further comprising stopping the reaction by adding an acid solution.

6. The method of claim 1, wherein the solid item is a bed net or a portion thereof.

7. The method of claim 1 wherein the solid item is a swab.

8. The method of claim 7 wherein the swab is obtained from a wall onto which a type II pyrethroid may have been sprayed.

9. A solution-based method for detecting the presence of a type II pyrethroid in a bed net or portion thereof, comprising:

adding a solution comprising (i) a solvent, (ii) para-nitrobenzaldehyde or paracyanobenzaldehyde and (iii) a dinitrobenzene or triphenyltetrazolium chloride to a vessel containing a bed net or portion thereof that may comprise a type II pyrethroid;

adding an aqueous base to the vessel containing the bed net or portion thereof; and observing contents in the vessel containing the bed net or portion thereof for a colour change indicating presence of a type II pyrethroid in the bed net or portion thereof.

10. The method of claim 9, further comprising stopping the reaction by adding an acid solution.

\* \* \* \* \*